United States Patent
Halonen et al.

[11] Patent Number: 5,817,336
[45] Date of Patent: Oct. 6, 1998

[54] COMPOSITION CONTAINING SELEGILINE

[75] Inventors: Matti A. Halonen, Rusko; Ulla I. Leinonen, Turku; Seppo S. L. Parhi, Kiviniemi; Ilse M. Piippo, Parainen; Gunilla M. Örn, Turku, all of Finland

[73] Assignee: Orion-Yhtymä Oy, Espoo, Finland

[21] Appl. No.: 774,892

[22] Filed: Dec. 27, 1996

Related U.S. Application Data

[63] Continuation of Ser. No. 347,293, Dec. 1, 1994.

[30] Foreign Application Priority Data

Apr. 2, 1993 [SE] Sweden .................................. 9301112

[51] Int. Cl.⁶ .......................... A61K 9/20; A61K 31/135; A61K 31/13
[52] U.S. Cl. ............................................ 424/465; 514/654
[58] Field of Search .............................. 424/465; 514/654

[56] References Cited

U.S. PATENT DOCUMENTS

| | | | |
|---|---|---|---|
| 4,812,481 | 3/1989 | Reischig et al. | 514/647 |
| 5,057,321 | 10/1991 | Edgren et al. | 424/413 |
| 5,128,145 | 7/1992 | Edgren et al. | 424/473 |
| 5,151,449 | 9/1992 | Milgram | 514/654 |
| 5,192,550 | 3/1993 | Edgren et al. | 424/473 |
| 5,192,808 | 3/1993 | Ruehl et al. | 514/654 |
| 5,276,057 | 1/1994 | Milgram et al. | 514/646 |
| 5,382,601 | 1/1995 | Nurnberg et al. | 514/775 |
| 5,384,312 | 1/1995 | Schirlin et al. | 514/63 |
| 5,387,615 | 2/1995 | Milgram et al. | 514/654 |

FOREIGN PATENT DOCUMENTS

| | | |
|---|---|---|
| 0 146 363 | 12/1984 | European Pat. Off. . |
| 146363A2 | 6/1985 | European Pat. Off. . |
| 241809A1 | 10/1987 | European Pat. Off. . |
| 0 294 441 | 12/1988 | European Pat. Off. . |
| 509761A1 | 10/1992 | European Pat. Off. . |
| 3710966 | 12/1987 | Germany . |
| 1153578 | 5/1969 | United Kingdom . |
| 2245559 | 1/1992 | United Kingdom . |
| WO 90/01928 | 3/1990 | WIPO . |
| 91/16885 | 11/1991 | WIPO . |
| 93/12775 | 7/1993 | WIPO . |

OTHER PUBLICATIONS

Lewis et al EXPO Congr. Int. Technol. Pharm. 3rd vol. 5 12–20 (1983) Hydrogenated Costa Oil to Replace Stearic Acid Stearate pp. 39–40.

Kalantzis et al GA. 117:137531 (p. 34) of Pharmakeutike 5(1):35–40 1992 Sodium Benzoate.

Edgren et al CA. 116:46325 of U.S. 5057321 (101591) p. 35 Ethoxylated Castor Oil.

Gross et al GA.114: 150U86 of Pharm. Acta Helv. 66(1):11–15(1991) pp. (35–36) Sodium Benzoate.

Daunora GA. 97: 203230 of U.S. 4347235 Aug. 31, 1982 p. 40 PEG/Na Propionate.

Johnson & Johnson CA. 85.99195 of Jpn 51019116 (21676) p. 40 PEG.

Oldani et al CA. 74: 15733 of Ger DE 2019658 (Nov. 5, 1970). p. 41 PEG.

*Primary Examiner*—Shep K. Rose
*Attorney, Agent, or Firm*—Burns, Doane, Swecker & Mathis, L.L.P.

[57] ABSTRACT

A new stable solid composition suitable for oral administration comprising a pharmaceutically acceptable acid addition salt of selegiline is achieved by reducing the destabilizing effect of the conventional lubricant present in such compositions, magnesium stearate either by replacing all or a substantial part of the magnesium stearate by other lubricants such as fatty acid esters and vegetable oils and/or by adding a pharmaceutically acceptable acid to the selegiline-containing tablets.

15 Claims, No Drawings

COMPOSITION CONTAINING SELEGILINE

This application is a continuation, of application Ser. No. 08/347,293, filed December 1, 1994, which is a 371 of PCT/FI94/00128.

The invention relates to a new stable composition suitable for oral administration comprising a pharmaceutically acceptable acid addition salt of selegiline e.g. the hydrochloride.

Selegiline ((-) N-(1 -phenyl isopropyl)-N-methyl-N-propionyl amine) is a MAO-B inhibitor. It has been available for more than ten years as an anti-Parkinson's disease drug.

The most common composition of selegiline is a tablet having the following main constituents: selegiline hydrochloride, a diluent e.g. lactose and starch, a binder such as polyvinyl pyrrolidone and a lubricant, usually a stearic acid salt e.g. magnesium stearate (EP 146363, WO 90/01 9289).

Australian Patent No. 71541/87 lists a large number of auxiliary agents useful in a synergic composition of selegiline and amantadine. Among these are mentioned vegetable oils (e.g. arachis oil, castor oil, olive oil, sesame oil, cotton seed oil, corn oil, wheat germ oil, sunflower seed oil, cod liver oil, mono-, di-, and triglycerides of saturated fatty acids $C_{12}$ to $C_{18}$). The only solid composition described contains 0.1 kg of magnesium stearate to 0.75 kg of selegiline hydrochloride.

European Patent No. 294 441 discloses a composition to prevent seasickness which comprises an active ingredient such as selegiline hydrochloride. The composition may contain an acceptable lubricating agent, such as stearic acid or a salt thereof, and may contain flavourants which are conventional additives of sweet industry, such as citric acid, tartaric acid and lactic acid. Example 1 describes pastilles weighing 1.3 g and containing 10 mg of selegiline hydrochloride, 7 mg of magnesium stearate and 13 mg tartaric acid.

The invention relates to a new stable solid composition suitable for oral administration comprising a pharmaceutically acceptable acid addition salt of selegiline e.g. selegiline hydrochloride. It was observed during long term stability studies of different formulations of selegiline hydrochloride that tablets containing magnesium stearate are not stable. Under stressed conditions i.e. heat (60° C.) combined with humidity (relative humidity of 75%), the instability increases i.e. the content of selegiline hydrochloride decreases.

The present invention overcomes the destabilizing effect of stearic acid salts by decreasing the amount of magnesium stearate below a certain level, e.g. by replacing all or a substantial part of the magnesium stearate with another lubricant such as a fatty acid ester, polyethylene glycol, colloidal silicon dioxide or vegetable oil.

The destabilizing effect of stearic acid salts may also be overcome by adding a pharmaceutically acceptable acid to the composition. Such a composition may contain a stearic acid salt or may be void of such salts.

The invention provides a solid composition suitable for oral administration (i.e. tablets, granules or capsules containing granules or powders) of a pharmaceutically acceptable acid addition salt of selegiline which is substantially free of stearic acid salts. By the expression substantially free of steric acid salts it is meant that the total amount of the stearic acid salt present in the composition (calculated as magnesium stearate or equivalent amount of the other stearic acid salt) is not more than 1 part by weight per 10 parts of selegiline hydrochloride (or equivalent amount of the other acid addition salt of selegiline), especially preferably per 25 parts of selegiline hydrochloride.

In one embodiment according to the invention the stearic acid salt is replaced with another lubricant. Examples of suitable groups of lubricants are esters of fatty acids and vegetable oils. It is a prerequisite for an effective lubricant that it does not melt during the manufacture of the composition. Accordingly, the fatty acid is preferably a saturated carboxylic acid of from 6 to 24 carbon atoms, most preferably 12 to 20 carbon atoms. The ester may be a mono-, di-or tri-ester of 1 to 10 carbon atoms, preferably of 2 to 4 carbon atoms. Preferred fatty acid esters which may be used as lubricants include triglycerids of saturated fatty acids or their mixtures e.g. glyceryl tristearates, glyceryl tripalmitates, glyceryl trimyristates, glyceryl tribehenates (sold under the trade name Compritol) and glyceryl paimitostearic acid ester. Instead of fatty acid esters it is also possible to use high melting fatty acids, for example stearic acid. Long chained polyethylene glycols are most preferred (e.g. those ones sold under trade name Macrogol 6000 or 20000). Suitable vegetable oils include solid oils such as cotton seed oil (sold under the trade names Sterotex or Lubritab) and castor seed oil (sold under trade name Cutina HR).

In another embodiment according to the invention the instability of the oral compositions containing stearic acid salts is avoided by adding one or more acids to such compositions. It is preferable to use pharmaceutically acceptable acids which are easily formulated into a solid oral composition, however, liquid acids may also be used. The acid may be organic or inorganic, although organic acids are preferred. Acids having $pK_a$ value below 5.88, preferably below 5 and most preferably below 3 are suitable. Accordingly, preferred acids are di-or tri-basic organic acids, having up to 10 carbon atoms, preferably up to 6 carbon atoms, for example tartaric acid, maleic acid, malic acid, fumaric acid and citric acid.

In a further embodiment according to the invention the two earlier embodiments are combined i.e. stearic acid salts are replaced with a fatty acid or vegetable oil and a pharmaceutically acceptable acid is added to the oral composition.

In addition to the active ingredients (a pharmaceutically acceptable acid addition salt of selegiline and possible other active ingredients) and the lubricant, the composition according to the invention may comprise other common additives such as a binder and a pharmaceutically acceptable diluent. There may also be other common excipients present, for example disintegrants, glidants, colours, flavours and sweeteners. Selegiline hydrochloride is preferably present in an amount of 2.5 mg to 100 mg per unit dosage. The amount of the other components may vary depending on their type and relative proportions. Accordingly, for compositions wherein selegiline hydrochloride is the only active ingredient, the amount of the lubricant may be about from 0.1 to 60 weight percent, the amount of the binder may vary about from 0 to 20 weight percent and the amount of the diluent is usually about from 1 to 95 weight percent. If a pharmaceutically acceptable acid and stearic acid salt are both present, the pharmaceutically acceptable acid is present in an amount which is at least equivalent to the amount of the stearic acid salt present, and preferably in excess.

The composition according to the invention may be prepared by conventional methods, e.g. the tablets may be manufactured using the direct compression method in which the ingredients are sieved and mixed in a suitable blender until homogenous and tabletted. It is also possible to capsulate the powder blend in gelatine capsules. The granulation method can also be used. The powders are sieved, mixed in a suitable mixer/granulator, moistened with a liquid until granules are formed. The granules are dried, suitable ingredients are added and the granules are tabletted or capsulated. The following examples illustrate how the compositions according to the invention may be prepared. However, it should be understood that a person having average skill in the art will be capable of modifying the compositions in several different ways.

COMPATIBILITY TESTS

The chemical compatibility of selegiline hydrochloride with different lubricants and fumaric acid was tested by mixing the raw materials (1:1), pressing tablets weighing about 500 mg, stressing one part of the tablets (one week at 60° C. and 75% relative humidity) and analysing the selegiline hydrochloride content of stressed and unstressed tablets. The results are given in the Table 1.

TABLE 1

Compatibility of different excipients with selegiline hydrochloride

| Excipient | Content of selegiline hydrochloride % | |
|---|---|---|
|  | unstressed | stressed |
| Magnesium stearate | 95 | 88 |
| Compritol | 98 | 96 |
| Lubritab | 98 | 97 |
| Fumaric acid | 100 | 98 |

Preparation of the compositions

Tables 2, 3 and 4 show different compositions of selegiline hydrochloride according to the invention: In table 2 magnesium strearate is replaced with glyceryl tribehenate (Compritol) and in table 3 with cotton seed oil (Sterotex). In table 4 a pharmaceutically acceptable acid (citric acid) is added keeping the amount of magnesium stearate at the same level as that of the conventional oral compositions.

The compositions were prepared as follows: Selegiline hydrochloride, lactose (or mannitol and maize starch, respectively) and polyvidone were sieved and mixed in a granulator. The powder blend was moistened and granulated with ethanol. The granules were dried and sieved. Microcrystalline cellulose, citric acid (when used) and the lubricant (Compritol, Sterotex and magnesium stearate, respectively) were sieved and mixed with the granules. The powder was tabletted using 6 mm (diameter) punches.

TABLE 2

A composition containing Compritol.

| Ingredient | weight, mg |
|---|---|
| Selegiline hydrochloride | 5.0 |
| Lactose | 57.0 |
| Polyvidon (Kollidon 30) | 7.0 |
| Ethanol | q.s. |
| Microcrystalline cellulose | 29.0 |
| Compritol | 5.0 |

When tablets containing 5 mg Compritol were stressed under the above given conditions the content of selegiline hydrochloride decreased only less than three percent (which is within the limits of the reproducibility of the analysis method) whereas it decreased more than 17 percent when similar conventional tablets containing 2 mg of magnesium stearate were stressed.

TABLE 3

A composition containing Sterotex.

| Ingredient | weight, mg |
|---|---|
| Selegiline hydrochloride | 5.0 |
| Mannitol | 40.0 |
| Maize starch | 40.0 |
| Polyvidone | 5.0 |
| Ethanol | q.s. |
| Microcrystalline cellulose | 28.0 |
| Sterotex | 5.0 |

When tablets containing 5 mg Sterotex were stresses under the above given conditions the content of selegiline hydrochloride decreased only less than three percent (within reproducibility limits) whereas it decreased more than 14 percent when similar conventional tablets containing 2 mg of magnesium stearate were stressed.

TABLE 4

A composition containing citric acid.

| Ingredient | weight, mg |
|---|---|
| Selegiline hydrochloride | 5.0 |
| Lactose | 57.0 |
| Polyvidon (Kollidon 30) | 7.0 |
| Ethanol | q.s. |
| Microcrystalline cellulose | 29.0 |
| Magnesium stearate | 2.0 |
| Citric acid monohydrate | 7.0 |

We claim:

1. A solid composition suitable for oral administration, comprising a pharmaceutically acceptable acid addition salt of selegiline, and a lubricant wherein the lubricant comprises a stearic acid salt in an amount of at least 0.1 weight percent based on the total weight of the composition, and the total amount of stearic acid salts present is not more than 1 part by weight per 10 parts of the selegiline hydrochloride or equivalent amount of other acid addition salt of selegiline.

2. The composition according to claim 1 wherein the total amount of stearic acid salts present is not more than 1 part by weight per about 25 parts of selegiline hydrochloride or equivalent amount of other acid addition salt of selegiline.

3. The composition according to claim 1 wherein the stearic acid salt is magnesium stearate.

4. The composition according to claim 1 wherein the pharmaceutically acceptable acid additive salt of selegiline is selegiline hydrochloride.

5. The composition according to claim 1 wherein the solid composition is a tablet.

6. The composition according to claim 1 wherein the selegiline is the only active ingredient.

7. A method for the treatment of Parkinson's disease comprising administering an effective amount of the composition of claim 1 to treat Parkinson's disease to a mammalian organism in need of such treatment.

8. A solid composition suitable for oral administration, comprising a pharmaceutically acceptable acid addition salt of selegiline, and a lubricant, wherein the lubricant is a fatty acid ester, polyethylene glycol or a vegetable oil in an amount of at least 0.1 weight percent based on the total weight of the composition and optionally stearic acid salts, wherein the total amount of stearic acid salts is not more than 1 part by weight per 10 parts of selegiline hydrochloride or equivalent amount of other acid addition salt of selegiline.

9. The composition according to claim 8 wherein the fatty acid ester is a triglyceride ester of a saturated fatty acid.

10. The composition according to claim 9 wherein the ester is glycerol tribehenate.

11. The composition according to claim 8 wherein the vegetable oil is cotton seed oil.

12. The composition according to claim 8 wherein the pharmaceutically acceptable acid additive salt of selegiline is selegiline hydrochloride.

13. The composition according to claim 8 wherein the solid composition is a tablet.

14. The composition according to claim 8 wherein the selegiline is the only active ingredient.

15. A method for the treatment of Parkinson's disease, comprising administering an effective amount of the composition of claim 8 to treat Parkinson's disease to a mammalian organism in need of such treatment.

* * * * *